(12) United States Patent
Vilhelmsson (10) Patent No.: US 7,233,402 B2
(45) Date of Patent: Jun. 19, 2007

(54) MEASUREMENT DEVICE FOR OPTICAL MEASUREMENT OF A PROPERTY OF A MEASUREMENT OBJECT

(75) Inventor: Kennet Vilhelmsson, Öjersjö (SE)

(73) Assignee: Alfa Exx AB, Partille (SE)

( * ) Notice: Subject to any disclaimer, the term of this patent is extended or adjusted under 35 U.S.C. 154(b) by 217 days.

(21) Appl. No.: 11/002,679

(22) Filed: Dec. 3, 2004

(65) Prior Publication Data
US 2005/0122526 A1    Jun. 9, 2005

(30) Foreign Application Priority Data
Dec. 5, 2003    (SE) .................................. 0303263

(51) Int. Cl.
*G01B 9/02*    (2006.01)
(52) U.S. Cl. ................................... 356/519
(58) Field of Classification Search .............. 356/4.09, 356/28.5, 445, 454, 480, 519
See application file for complete search history.

(56) References Cited

U.S. PATENT DOCUMENTS

| 3,733,129 | A | * | 5/1973 | Bridges | ..................... 356/5.09 |
| 3,901,597 | A | | 8/1975 | White | |
| 4,837,428 | A | * | 6/1989 | Takagi et al. | ................ 250/205 |
| 5,069,545 | A | | 12/1991 | Hinz | |
| 5,541,946 | A | | 7/1996 | Scheps et al. | |
| 5,646,396 | A | * | 7/1997 | Richard | ....................... 250/216 |
| 6,529,542 | B1 | | 3/2003 | Karlsen et al. | |
| 6,658,031 | B2 | * | 12/2003 | Tuganov et al. | ............... 372/34 |
| 7,016,046 | B2 | * | 3/2006 | Hauger | ....................... 356/479 |
| 2004/0004751 | A1 | * | 1/2004 | Vilhelmsson | ................ 359/245 |

* cited by examiner

*Primary Examiner*—Gregory J. Toatley, Jr.
*Assistant Examiner*—Michael A. Lyons
(74) *Attorney, Agent, or Firm*—Harness, Dickey & Pierce, P.L.C.

(57) ABSTRACT

This invention relates to a measurement device, for optically measuring a property of a measurement object, the measurement device comprising a main resonator having a first and a second reflecting end defining a cavity having an effective optical cavity length, an optical gain element for generating light travelling along an optical beam path between the first and second reflecting ends, and a dispersive focusing resonator element which is positioned along the optical beam path between the optical gain element and the second reflecting end, whereby the measurement object is arranged to be at least partly positioned within the optical beam path of the main resonator, and whereby the measurement device further comprises a detection means for detecting a characteristic of light emitted from the main resonator, the value of the detected characteristic being a measure of a property of the measurement object.

16 Claims, 4 Drawing Sheets

MEASUREMENT DEVICE FOR OPTICAL MEASUREMENT OF A PROPERTY OF A MEASUREMENT OBJECT

PRIORITY STATEMENT

This application claims priority from Swedish Patent Application No. 0303263-8, filed on Dec. 5, 2003, in the Swedish Intellectual Property Office, the disclosure of which is incorporated herein in its entirety by reference.

TECHNICAL FIELD OF THE INVENTION

The present invention relates to a measurement device for optical measurement of a property of a measurement object.

BACKGROUND ART

There are many measurement devices for optically measuring a property of a measurement object available on the market today. For example measurement devices using laser are used in various applications such as chemical analysis, spectroscopy, optical disc readers, and metrology.

One such measurement device for measuring small distances and other physical parameters which are capable of altering an optical path length is described in GB 1038140. The device comprises a He—Ne laser, an external reflector which is aligned with the laser, and a photo detector. The reflector is movable so that the phase of the reflected light returned into the laser may be adjusted in relation to the light emitted from the laser, whereby the generation of laser light is intensified or counteracted, respectively. The generation is detected by the photo detector, whereby the reading of the photo detector is periodical having the period $\lambda/2$. Thus, the movements of the external reflector, i.e. the change in optical length between the laser and the reflector, may be determined from the readings of the photo detector.

However, a problem with the measurement device disclosed in GB 1038140, as well as with other known measurement devices, is that it due to the construction is sensitive to misalignments, especially misalignment of the external reflector, and at the same time quite expensive to manufacture and difficult to control. Moreover, the reading in GB 1038140 is periodical, i.e. non-monotone, whereby it is not possible to directly obtain an absolute measurement of for example the distance.

SUMMARY OF THE INVENTION

An object of the present invention is to provide a measurement device which is improved compared with known measurement devices.

A particular object is to provide a measurement device which may be realised in a cost-efficient fashion, and that is easy to control.

These and other objects are achieved by a measurement device for optically measuring a property of a measurement object, which measurement device comprises a main resonator having a first and a second reflecting end defining a cavity having an effective optical cavity length, an optical gain element for generating light travelling along an optical beam path between the first and second reflecting ends, and a dispersive focusing resonator element, being positioned along the optical beam path between the optical gain element and the second reflecting end, whereby the measurement object is arranged to be at least partly positioned within the optical beam path of the main resonator, and whereby the measurement device further comprises a detection means for detecting a characteristic of light emitted from the main resonator, the value of the detected characteristic being a measure of a property of the measurement object.

The invention is based on the understanding that the measurement object affects the effective cavity length of the main resonator and/or the resonator loss, whereby a characteristic of the light emitted from the resonator is affected due to the properties of the dispersive focusing element. The characteristic of the light emitted may according to the invention vary monotonically when the effective cavity length and/or resonator loss is changed. Thereby, an easy to control and easy to read measurement device may be achieved. Moreover, because of the simple construction, the measurement device may be less costly to manufacture.

Also, the measurement according to the invention is resonant since the measurement takes place inside the main resonator, whereby the effective measurement distance becomes very long. Thus, it is due to the inventive arrangement possible to achieve a measurement device having a long active measurement length, but still having a small physical size, which enhances the usefulness.

Preferably, the characteristic of light which is to be detected by the detection means is at least one of the wavelength, the power, the polarisation, and the phase of the emitted light.

In one embodiment of the invention, the object to be measured is a solid object. Preferably, the measurement object constitutes the second reflecting end of the measurement device. Thus, the measurement object acts as a feedback element and reflects light back in the resonator cavity. The measurement device according to this embodiment may for example be used to measure a position of the measurement object. The position of the measurement object affects the effective optical cavity length of the main resonator, which in turn affects a characteristic of the light emitted from the resonator, whereby that characteristic is a measure of the position of the measurement object.

Also preferably, the measurement object and the rest of the measurement device may be arranged to be moved in relation to each other in a direction which is essentially perpendicular to the direction of the optical beam which is reflected by the measurement object, i.e. in a plane normal to the beam. Thus, the measurement object may be moved, while the remaining measurement device is held essentially fixed. Alternatively, the remaining measurement device is moved, while the measurement object is held essentially fixed. As a further alternative, both the measurement object and the remaining measurement device are moved in relation to the surroundings.

By moving the measurement object and the rest of the measurement device in relation to each other, an object having a surface relief may advantageously be measured. The surface relief causes the effective optical cavity length of the main resonator to change, whereby the characteristic of the emitted light is changed due to the properties of the dispersive focusing resonator element, and whereby the value of a characteristic of the emitted light is a measure of the surface relief. This enables for a simple and feasible measurement device, which for example may be used in a scanning microscope. The measuring device according to this embodiment may also advantageously be used as a pickup in for example a CD-player, DVD-player or CD-ROM-player, in order to read the data track on the disc. In this case, no movement of the pickup in relation to wobbling compensation is necessary since the pickup according to the invention is essentially self-aligning. Thus, the pickup may be constructed with less movable parts, which for example facilitates manufacturing and ensures a stable operation. Also, the pickup may advantageously be arranged to simultaneously read information from multiple layers, for example on a double-layered optical disc.

According to another embodiment of the invention, the measurement object is for example a gas, a liquid or a particle aerosol, which is arranged to flow through the optical beam path of the main resonator. The flow may have a flow velocity of 0 m/s or more, depending on the application. The flow of the measurement object affects the effective optical cavity length of the main resonator, whereby a characteristic of the light emitted from the resonator changes. The change in for example the wavelength or the power of the emitted light may be detected by the detection means. The measurement device may advantageously be used for several types of measurements, for example for measuring the presence of a measurement object.

In a further embodiment of the invention, the measurement device also comprises an adjustable driver for energising the main resonator, and a current detection device for detecting the current used by the driver. When a measurement object affects the resonator losses, the light emitted from the main resonator will change, whereby the driver is adjusted so that the power of the emitted light is held constant, and whereby the current used by said adjustable driver is a measurement of a property of the measurement object. Further, by moving the second reflecting end, for example a mirrored element, the measurement device may be configured to operate at certain wavelengths, and/or to scan over a wide range of wavelengths, for example to determine at what wavelength(s) resonator losses occur, whereby the losses may be a result of for example absorption and/or scattering. The measurement device according to this embodiment may advantageously be used to detect for example the content or the concentration of a known measurement object, or to detect what substance or substances that are present in a mixture, as well as the concentrations of the substances in a mixture.

Preferably, the light which is to be detected by the detection means is emitted from at least one of the first and the second reflecting end of the main resonator.

BRIEF DESCRIPTION OF THE DRAWINGS

Currently preferred embodiments of the invention will now be further described in reference to the accompanying drawings wherein.

DETAILED DESCRIPTION OF PREFERRED EMBODIMENTS OF THE INVENTION

Figure 1:
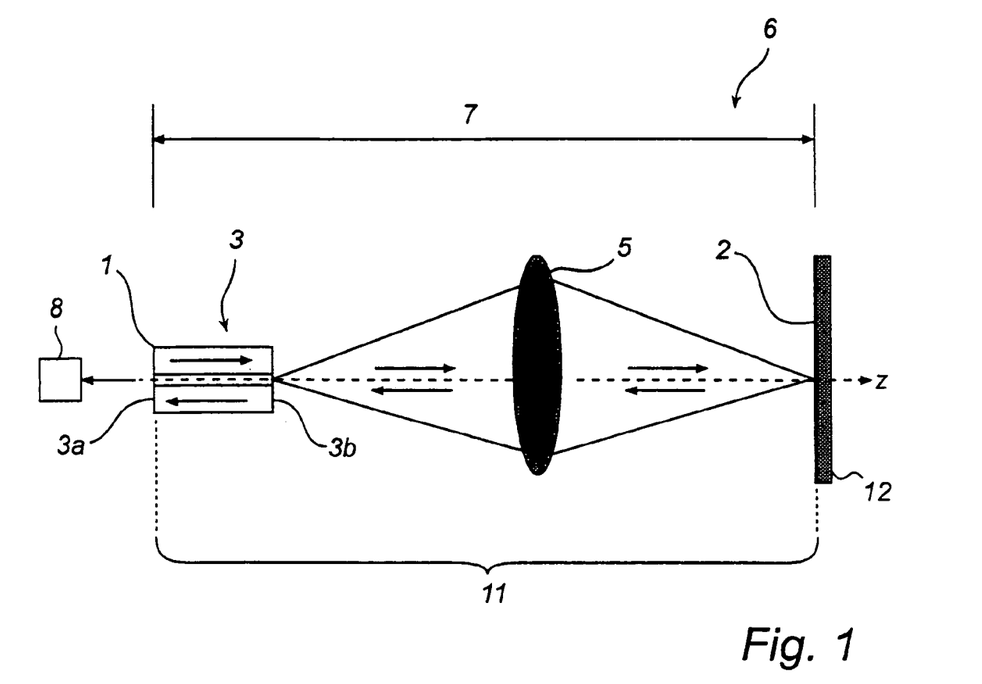
FIG. 1 schematically shows a measurement device according to a first alternative of a first embodiment of the present invention.

A first alternative of a first embodiment of the present invention is disclosed in FIG. 1. FIG. 1 shows a measurement device 6 comprising a main resonator 11 having a first and a second reflecting end 1, 2, defining a cavity 7, whereby the second reflecting end 2 is constituted by a measurement object 12 for which a property is to be measured. An optical gain element 3 is arranged within the resonator cavity 7. The optical gain element 3 may be for example an edge emitting semiconductor element as in FIG. 1. Alternatively, the optical gain element may be a surface emitting semiconductor element.

The term edge emitting semiconductor element is to be construed as an optical gain element in which a light beam propagates in a direction that is essentially perpendicular to the surface normal of the epitaxial layers that constitute the active material of the optical gain element. The term surface emitting semiconductor element is to be construed as an optical gain element in which a light beam propagates in a direction that is essentially parallel to the surface normal of the epitaxial layers that constitute the active material of the optical gain element.

The optical gain element has a first and a second opposed end surface 3a, 3b, whereby the first end surface 3a in this case is arranged to constitute the first reflecting end 1 of the main resonator 11.

Figure 2:
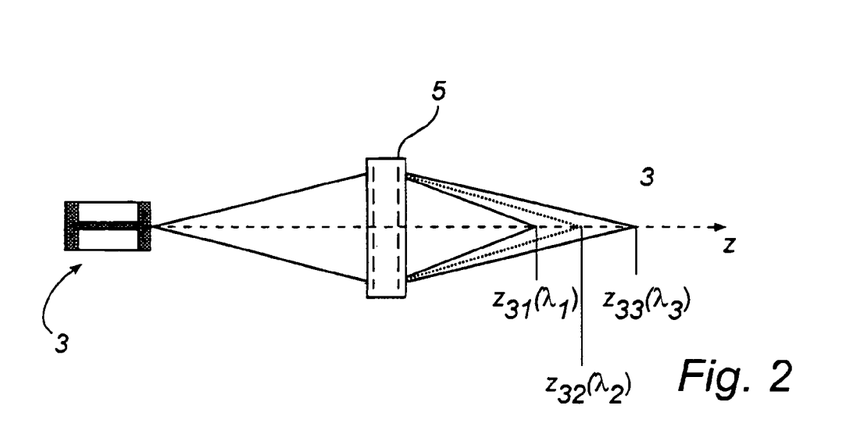
FIG. 2 schematically shows the working principle for the invention.

The measurement device 6 further comprises a dispersive, focusing element 5, which is arranged within the cavity between the second end surface 3b of the optical gain element 3 and the second reflecting end 2 of the cavity, i.e. the measurement object 12. The dispersive, focusing element 5 exhibits a wavelength dependent focal distance, which generates a wavelength dependent position of an image plane, as indicated in FIG. 2. In FIG. 2, it is schematically shown that light having a first wavelength $\lambda 1$ is focused in a first plane, light having a second wavelength $\lambda 2$ is focused in a second plane, and light having a third wavelength $\lambda 3$ is focused in a third plane. Thus, for example a reflecting element positioned in the first plane will reflect light having the wavelength $\lambda 1$. The dispersive, focusing element 5 may for example be constituted by a refractive and a diffractive element. The structure of the dispersive, focusing element 5 will further be described below.

Again referring to FIG. 1, the measurement device 6 also includes a detection means 8. The detection means 8 in this case is arranged adjacent to the main resonator 11 in order to detect a characteristic of light, for example the wavelength, the power, the polarisation or the phase of the light emitted from the main resonator. The detection means 8 may for example be a wavelength detector or a light intensity detector depending on the characteristic to be measured.

As a result of the properties of the dispersive, focusing element 5 mentioned above, by moving the measurement object between different longitudinal positions, i.e. along the optical beam path of the resonator, and thereby varying the effective length of the cavity 7, the measurement device 6 may be arranged to emit light with different wavelengths, whereby light emitted having a certain wavelength uniquely corresponds to a certain longitudinal position of the measurement object. The dispersive, focusing element enables a high Q value for the resonator, i.e. small losses for a narrow wavelength interval for every position of the measurement object.

Consequently, a measurement of the position of the measurement object along the z-axis is achieved by detecting the wavelength which corresponds to the image plane at a distance from the dispersive, focusing element 5 in which plane the reflecting surface of the measurement object is positioned. The wavelength may be made to vary monotonically with respect to the movement of the measurement object.

The measurement may be carried out over a relatively large distance range (and hence wavelength range) without causing mode hops in the resonator. This is due to the fact that the dispersive focusing element 5 is formed so that the waist of a mode in the resonator moves with the same velocity as the stretch of the nodal pattern along the optical axis of the cavity, whereby the total phase shift in the resonator is held constant at movement of the measurement object, which means that mode hops are avoided. The wavelength range of the measurement device according to the invention is only limited by the bandwidth of the optical gain element.

Preferably, the light is coupled out through the first reflecting end 1 of the main resonator 11, i.e. in this case through the first end surface 3a of the optical gain element 3, whereby the light may be detected by the detections means 8 arranged adjacent to the cavity. Further, a certain wavelength detected by the detection means 8 corresponds to a certain length of the main resonator cavity 7. As described above, the main resonator 11 in this case is defined by the first reflecting end 1 and the measurement object 12, thus the absolute position of the measurement object may easily be obtained. The measurement device 6 may also be used for continuous measuring, whereby a change in wavelength detected by the detection means 8 corresponds to a change in relative position between the measurement object and the measurement device.

The measurement device according to this first alternative of the first embodiment may be used in several applications relating to for example detecting distances to a measurement object or detecting an unknown surface topography. The latter may be achieved by moving the measurement object in the x-y-plane in relation to a measurement device, whereby the surface relief may be detected. Alternatively, the measurement device is moved in the x-y-plane in relation to the measurement object. For example, the device may be used in a scanning microscope in which the measurement device is swept over a measurement object. The wavelengths reflected by the surface of the object are then detected by the detection means, whereby the variations in resonant wavelength becomes a measure of the surface topography, which may be used to display a magnified image of said object.

Figure 3:
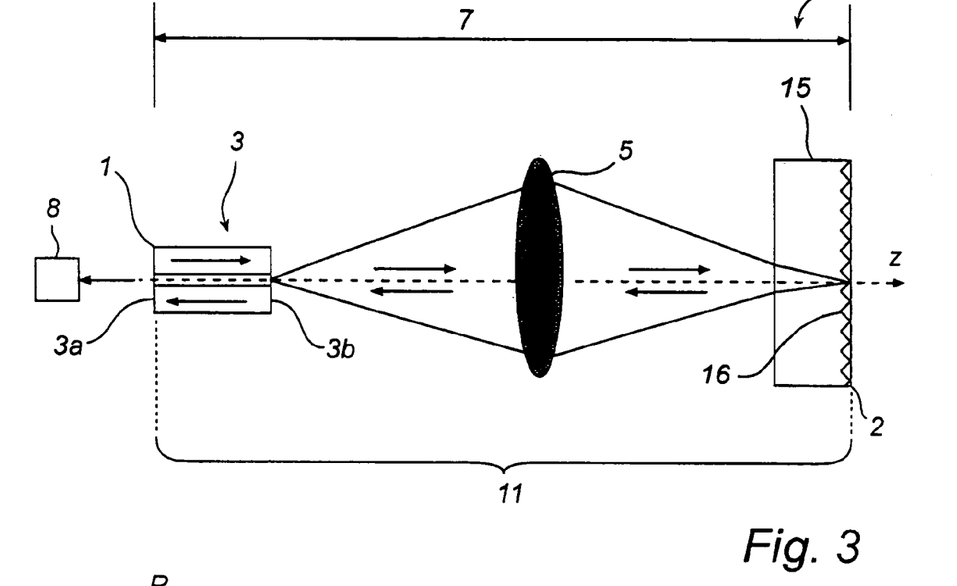
FIG. 3 schematically shows a measurement device according to a second alternative of a first embodiment of the present invention.

According to a second alternative of the first embodiment of the invention, the measurement device may be used as a pickup in an optical disc player, for example a compact disc (CD) player, a digital versatile disc (DVD) player, or a CD-ROM player. An arrangement according to this second alternative of the first embodiment is schematically shown in FIG. 3. FIG. 3 shows a main resonator 11 having a first and a second reflecting end 1, 2, defining a cavity 7, whereby the second reflecting end 2 is constituted by a measurement object, in this case a CD 15. An optical gain element 3, for example an edge emitting semiconductor element as described above in relation to the first alternative of this first embodiment, is arranged within the resonator cavity. Alternatively, a surface emitting semiconductor element may be used as an optical gain element. The optical gain element 3 has a first and a second opposed end surface 3a, 3b, whereby the first end surface 3a in this case is arranged to constitute the first reflecting end 1 of the main resonator 11.

The measurement device 6 further comprises a dispersive, focusing element 5, which is arranged within the cavity 7 between the second end surface 3b of the optical gain element 3 and the measurement object. The dispersive, focusing element 5 exhibits a wavelength dependent focal distance, which generates a wavelength dependent position of an image plane, as shown in FIG. 2. The dispersive, focusing element 5 may for example be constituted by a refractive and a diffractive element.

The measurement device in FIG. 3 also includes a detection means 8. The detection means 8 is arranged adjacent to the main resonator 11 in order to detect a property of light emitted from the main resonator. The detection means may for example be a photo-diode, which detects the power, and/or a wavelength detection device.

The measurement object, i.e. the CD 15, contains data stored in digital form. The digital data is represented by small cavities forming a surface relief 16 embedded in the disc. The cavities are arranged in a helical data track on the disc. A cavity represents a first data value, and a non-cavity area on the data track represents a second data value.

The disc is positioned in relation to the measurement device so that a cavity represents a different longitudinal position along an optical beam path of the resonator compared to a non-cavity. Thereby, as a result of the properties of the dispersive, focusing element 5 as mentioned above, a cavity and a non-cavity will reflect light having different wavelengths, which wavelengths corresponds to an image plane at a distance along the z-axis from the dispersive, focusing element respectively. Thus, a first wavelength represents cavities and a second wavelength represents non-cavities.

It should be noted here that when focusing the light in order to read the CD-track, the focused reading area of the light covers more than the width of a cavity of the track. This means that when the reading light is in position at a cavity, a first part of the light will be reflected in the cavity, and a second part of the light will be reflected by the area of the disc surrounding the cavity. This means that the first part of the reflected light will due to the dispersive focusing element have a certain wavelength, while the second part of the reflected light will have another wavelength. Thus, in areas with cavities, different transverse parts of the resonator mode sees different phase shifts which effectively increases the cavity loss and results in decreased output power of the resonator.

Figure 4A:
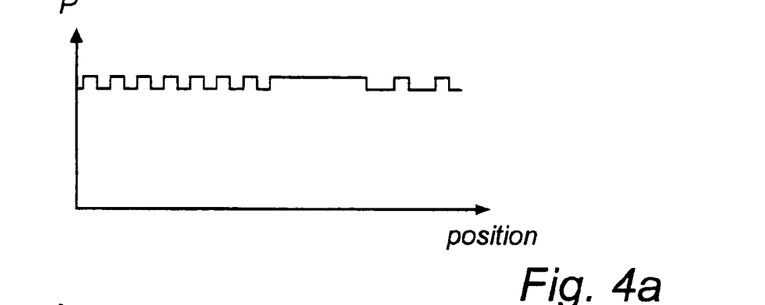
FIGS. 4a–4b schematically show diagrams of output data generated by the measurement device in FIG. 3.

Consequently, a reproduction of the data on the optical disc may be achieved by detecting the power of the light emitted from the resonator and translating the output to ones and zeros, whereby the string of ones and zeros then may be decoded and demodulated and converted to for example music. The power output in relation to the position of the disc is schematically shown in FIG. 4a.

Preferably, the light is coupled out through the first reflecting end 1 of the main resonator 11, i.e. in this case through the first end surface 3a of the optical gain element 3, whereby the power of the emitted light may be detected by the detection means.

Again referring to FIG. 2, light having a wavelength $\lambda 1$ is focused in a plane $z_{31}$, and light having a wavelength $\lambda 3$ is focused in a plane $z_{33}$. The maximum range $z_{31}$–$z_{33}$ depends on the bandwidth of the optical gain element. In a preferred arrangement, the range $z_{31}$–$z_{33}$ is much larger than the depth of a cavity on the optical disc which is to be read by the pickup. Depending on the position of the disc along the z-axis, different wavelengths and hence power levels will be detected by the pickup as described above. However, the relative difference between the power generated by a cavity and the power generated by a non-cavity is essentially the same for all positions, which means that reproduction of the data on the optical disc may be achieved. Consequently, the disc may be positioned at any location within the range $z_{31}$–$z_{33}$ along the z-axis. This is schematically shown in FIG. 4$b$.

Figure 4B:
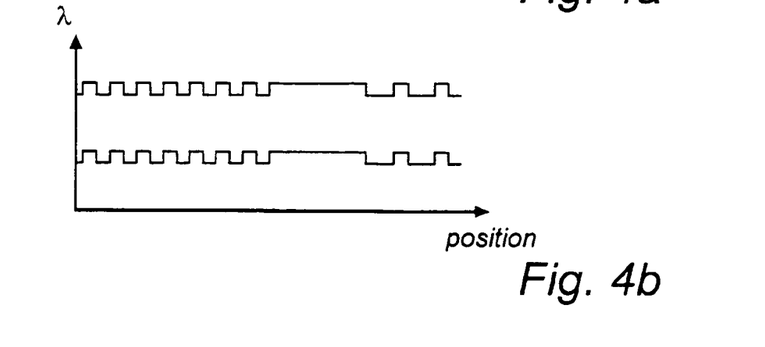

In FIG. 4$b$, two different schematic data signals detected by the detection means are illustrated. The y-axis indicates the wavelength or the axial position of the disc, while the x-axis label "position" refers to the position along the data track on the disc surface. Even though the two signals are at different wavelength levels (indicating two different locations of the disc along the z-axis), they will still generate essentially the same output to the optical disc player since the relative position of the first and second data values, e.g. ones and zeros, in the different data signals are the same. Thus, the pickup is self-aligning with respect to position along the z-axis in FIG. 3. The small changes in wavelength of the two curves in FIG. 4$b$ results in changes in power of the light, which represents the information on the disc, as described above.

The self-alignment is an advantage when it comes to wobbling compensation. Wobbling occurs when the disc is not completely flat, thus when the disc is spinning the distance between the disc and the pickup lens varies. In known optical disc players, a servo mechanism is typically used for moving the pickup towards and away from the disc in order to keep the focus, i.e. wobble compensation. However, by using a pickup according to the present invention, wobbling problems are avoided since the lens does not need to be moved in order to keep track of focus. Instead, the pickup is self-aligning and no servo mechanism is needed. This means that a pickup may be constructed with less movable parts, which results in a pickup that is more robust and easier to manufacture.

The pickup according to the invention may also advantageously be used to simultaneously read information from different layers on an optical disc. The layers, for example two layers on one side of the disc, represent different distances along the z-axis from the dispersive focusing element, whereby light reflected from the different layers will have different wavelengths, as described above. Given that the layers of the disc are sufficiently separated along the z-axis, the smaller wavelength changes and thus the corresponding power changes that the cavities give rise to may be extracted so that reproduction of the data on the optical disc may be achieved. Of course, the aspect of wobbling compensation may also be applied to this multiple layer reading.

Figure 5:
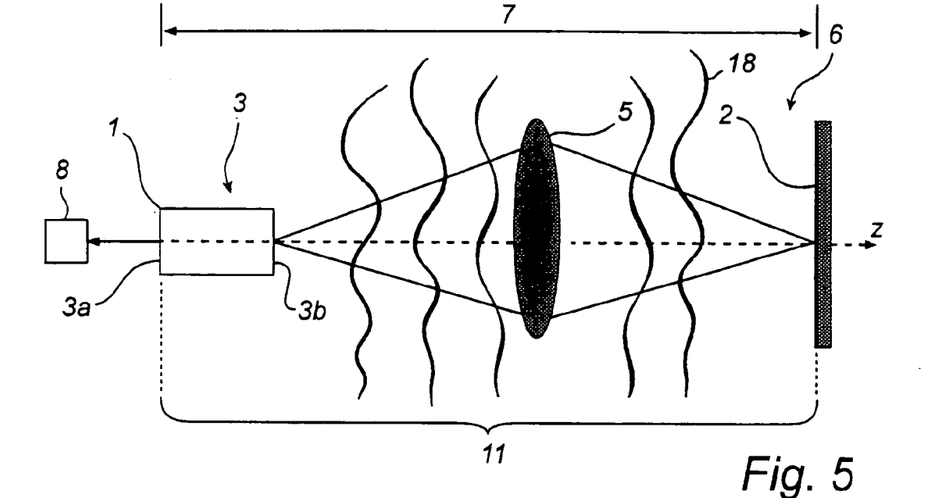
FIG. 5 schematically shows a second embodiment of the present invention.

A second embodiment of the present invention is shown in FIG. 5. FIG. 5 shows a measurement device 6 comprising a main resonator 11 having a cavity 7, which is defined by a first and a second reflecting end 1, 2. An optical gain element 3, for example an edge emitting semiconductor element as described above in relation to the first alternative of the first embodiment, is arranged within the resonator cavity 7. Alternatively, a surface emitting semiconductor element may be used as an optical gain element. The optical gain element 3 has a first and a second opposed end surface 3$a$, 3$b$, whereby the first end surface 3$a$ in this case is arranged to constitute the first reflecting end 1 of the main resonator 11. The measurement device further comprises a dispersive, focusing element 5, which is arranged within the cavity 7 between the second end surface 3$b$ of the optical gain element 3 and the second reflecting end 2. The dispersive, focusing element 5 exhibits a wavelength dependent focal distance, which generates a wavelength dependent position of an image plane, as indicated in FIG. 2. The dispersive, focusing element 5 may for example be constituted by a refractive and a diffractive element.

Again referring to FIG. 5, the measurement device 6 also includes a detection means 8. The detection means is arranged adjacent to the main resonator 11 in order to detect a property of light emitted from the main resonator. The detection means may for example be a wavelength detector.

In the measurement device according to this embodiment, a measurement object, for example a gas, a liquid or a particle aerosol is arranged to flow through the optical beam path of the main resonator 11, whereby the flow may have a flow velocity of 0 m/s or more. The measurement object may flow on either side of the dispersive, focusing element 5.

The reflecting end 2, which in this case may be constituted by for example a mirror element, is arranged at a fixed longitudinal position along the optical beam path of the resonator, whereby when no measurement object is present in the cavity, the resonator may be arranged to emit light having a constant wavelength. This constant wavelength may be detected by the detection means 8.

However, when the measurement object (for example a gas 18) is present in the main resonator, the presence and properties of the gas 18 causes the refraction index of the resonator medium to change. This in turn results in that the effective optical cavity length of the resonator changes, whereby the wavelength of the light emitted from the main resonator changes due to the dispersive, focusing element 5 as described above in relation to the first alternative of the first embodiment.

Consequently, the measurement device according to this embodiment of the invention may be used to detect the presence of a measurement object in the measurement device, whereby the presence is indicated by a change in wavelength or power of the light emitted from the resonator, which light is detected by the detection means 8. The measurement device of FIG. 5 may also be used to measure for example changes in pressure, temperature, and/or humidity etcetera that alters the refraction index in the resonator.

In FIG. 5, the light which is to be detected by the detection means 8 is coupled out through the first reflecting end 1 of the main resonator 11, i.e. through the first end surface 3$a$ of the optical gain element 3. For this variant, the second reflecting end 2 is arranged to be a reflecting broadband mirror, while the first end surface 3$a$ is arranged to transmit a desired predefined portion of the light which may be detected by the detection means. Alternatively, the light may be coupled out through the second reflecting end 2 of the main resonator. For this variant, the second reflecting end 2 is arranged to transmit a portion of the light which may be detected by the detection means.

Further, the reflecting end 2, for example a mirror element, may have a reflectance which varies over the cross section of the element in such a way that it is highly reflective for the main mode of the cavity, while having a lower reflectance for higher order modes. This results in spatial filtration, i.e. higher order spatial modes are suppressed, and the main mode of the cavity is favoured, which may be desirable for certain applications such as gas analysis. The above effect may be achieved by applying an anti-reflection coating, an absorbing layer, a spreading, light scattering layer, or a reflective or transmissive diffractive surface relief to the element area outside of a highly reflecting central area for the main mode.

Figure 6:
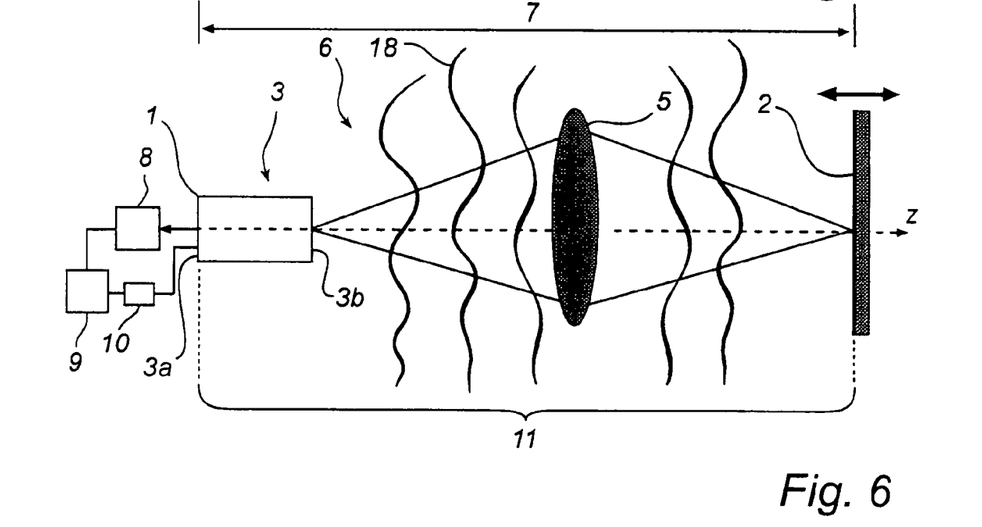
FIG. 6 schematically shows a third embodiment of the present invention.

A third embodiment of the invention is shown in FIG. 6. FIG. 6 shows a measurement device 6 comprising a main resonator 11 having a cavity 7, which is defined by a first and a second reflecting end 1, 2. The second reflecting end 2 may for example be a mirrored element having characteristics as described above in relation to the second embodiment. An optical gain element 3, for example an edge emitting semiconductor element as described above in relation to the first alternative of the first embodiment, is arranged within the resonator cavity 7. Alternatively, a surface emitting semiconductor element may be used as the optical gain element. The optical gain element 3 has a first and a second opposed end surface 3a, 3b, whereby the first end surface 3a in this case is arranged to constitute the first reflecting end 1 of the main resonator 11.

The measurement device further comprises a dispersive, focusing element 5, which is arranged within the cavity 7 between the second end surface 3b of the optical gain element 3 and the second reflecting end 2. The dispersive, focusing element 5 exhibits a wavelength dependent focal distance, which generates a wavelength dependent position of an image plane, as indicated in FIG. 2. The dispersive, focusing element 5 may for example be constituted by a refractive and a diffractive element.

Again referring to FIG. 6, the measurement device 6 also includes a detection means 8, which is arranged adjacent to the cavity in order to detect a property of light emitted from the main resonator, for example the wavelength and/or the power of the light. As in the second embodiment described above, the light may be coupled out through either the first reflecting end 1 of the main resonator 11, and/or the second reflecting end 2. The measurement device also comprises a driver 9, which is connected to the detection means 8, and to the optical gain element 3. The driver is arranged to energise the optical gain element 3, and to be adjustable in order to enable a variation in the driving current used to energise the optical gain element 3. Also, the measurement device comprises a current detection means 10, which is adapted to detect the current used by the driver 9.

In the measurement device according to this embodiment, a measurement object, for example a gas, a liquid or a particle aerosol, is arranged to be present in the optical beam path of the main resonator 11. The measurement object may flow through the resonator through the optical beam path, whereby the flow may have a flow velocity of 0 m/s or more, depending on the application. The measurement object may flow on either side of the dispersive, focusing element.

The embodiment of the invention shown in FIG. 6 is based on an understanding that a measurement object such as a gas, liquid or particle aerosol which is present in the resonator affects the resonator losses, whereby the power of the light passing through the measurement object, and thus the power of the light detected by the detection means, decreases.

The decrease in power may for example be caused by the fact that a gas, liquid or particle aerosol may absorb certain wavelengths of light.

The measurement device 6 according to this embodiment may for example be used to measure the content or concentration of a known measurement object. Before measurement of for example a known gas which absorbs light having a known wavelength (hereinafter indicated by $\lambda_{abs}$), the reflecting end 2 of the measurement device is adjusted by moving the reflecting end 2 to a certain longitudinal position along the beam path of the main resonator 11, thereby changing the effective optical length of the resonator so that the resonance wavelength of the measurement device corresponds to the wavelength $\lambda_{abs}$. The adjustment of the resonance wavelength is achieved in the same manner as described above in relation to the first alternative of the first embodiment. Because of the inventive arrangement, the tuning interval is relatively large, which enhances the usefulness of the measurement device. The interval in which the desired wavelength may be set is only limited by the bandwidth of the optical gain element. The wavelength emitted from the resonator may be monitored by the detection means 8.

Figure 7:
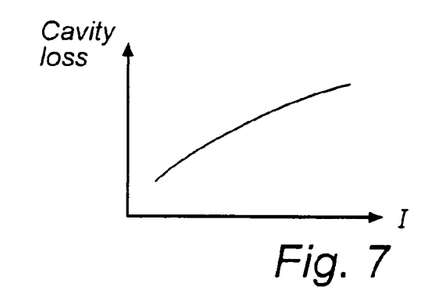
FIGS. 7–8 schematically show diagrams of output data generated by the measurement device in FIG. 6.

When a measurement object, here for example a gas 18, is present in the resonator, the resonator losses increase due to the absorption of the wavelength $\lambda_{abs}$. However, the driver 9 for energising the optical gain element 3 is controlled to adjust the drive current used to energise the optical gain element 3 so that the power of the emitted light is held essentially constant. This is achieved by a feedback loop between the driver 9 and the detection means 8. Thus, the change of the drive current of the gain element 3 compensates for the power loss of the light which is due to absorption by the gas, whereby the power of the emitted light is held essentially constant. The current used by said driver in order to keep the power of the emitted light at a constant level is then a measure of the concentration of the gas, as schematically shown in FIG. 7. The current used by the driver 9 is detected by the current detection means 10.

From FIG. 7 it should be understood that a higher current needed to keep the power of the emitted light at a constant level indicates a higher resonator loss, and thus a higher gas concentration. Preferably, the measurement device is calibrated prior to use in order to determine current-to-concentration ratios for different measurement objects.

It should be noted that the gas may be arranged to flow through the resonator, whereby it is possible to continuously measure the contents of the gas over time. It should also be noted that due to the resonant measurement according to the invention, the light travels through the measurement object multiple times, as if the measurement was made on a larger volume of the measurement object. This means that the size of the measurement device may significantly be reduced compared to a conventional device in which light is emitted from one side of the measurement object, travels through the measurement object, and is detected on the opposite side of the measurement object.

Figure 8:
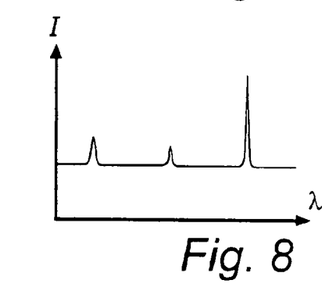

Also, the measurement device 6 according to this embodiment may be used to based on absorption analyse a mixture of for example gases in order to detect the kinds of gases that are present in said mixture. In this case, when the mixture is present in the resonator, the reflecting end 2 of the measurement device is moved longitudinally along the beam path of the main resonator 11 so that the measurement device as described above is adapted to emit light having wavelengths of corresponding range. When scanning the wavelength spectrum, certain wavelengths will be more or less absorbed by the different gases in the mixture, which results in losses in the power of the light at those wavelengths. These power losses are indicated by the increase of current used by the driver 9 to adjust the optical gain element 3 to keep the power of the emitted light constant at those wavelengths. The result of an illustrative scan is schematically shown in FIG. 8. By knowing what wavelengths that are absorbed by what gases, it is from FIG. 8 possible to determine what kinds of gases that are present in the subjected mixture.

Through the calibration of the measurement device, and by knowing the gain curve of the optical gain element, it is also possible to determine the absolute contents of the gases in the mixture based on the current-wavelength diagram.

It should be noted here that this proceeding also may be used to analyse a gas having several absorption wavelengths. It should also be noted that, in accordance with the present invention, the above mentioned scan may be performed over a wide range of wavelengths due to the properties of the focusing dispersive element 5. The scanning range is only limited by the spectral width of the optical gain element. This means that the measurement device may be used to detect and measure a wide range of different measurement objects.

The measurement device according to the third embodiment may also be used for measurements based on light scattering. This variant is based on an understanding that the particles in a measurement object such as a gas, liquid or particle aerosol exhibit wavelength dependent scattering. When for example a gas is subjected to light of a certain wavelength incident from a certain direction, the light is scattered. Thereby, the resonator losses varies, whereby the power emitted from the resonator changes. For example the larger concentration of a gas, the more light of a certain wavelength is scattered.

As above, when a measurement object, e.g. a gas 18, flows trough the main resonator 11 of the measurement device 6, the driver 9 is controlled to adjust the drive current of said optical gain element 3 so that the power of the emitted light is held essentially constant. Thus, the change of the drive current of the optical gain element compensates for the power loss of the light which is due to scattering by the gas, whereby the power of the emitted light is essentially constant.

The current used by said driver 9 in order to keep the power of the emitted light at a constant level is then detected by the current detection device 10, whereby the current is a measure of the property of the measurement object.

Again as above, this variant of the third embodiment may for example be used to measure the content or concentration of a known measurement object that scatters light having a known wavelength $\lambda_{scatter}$. In this case, the resonator is prior to use adjusted to resonate at this wavelength by adjustment of the reflecting end 2. The measurement device may also be used to detect what substance or substances that are present in a mixture, as well as the concentrations of the substances in a mixture, by scanning the wavelength spectrum to determine at what wavelengths light is scattered. The scanning may be carried out over a wide spectrum, which because of the inventive arrangement of the measurement device only is limited by the bandwidth of the optical gain element.

The dispersive, focusing element of the above embodiments will hereinafter be described in closer detail. According to a straight forward approach, the dispersive, focusing element is constituted by a single refractive positive lens element having both dispersive and focusing characteristics. The refractive index of the refractive element is dependent on the wavelength of the incident light, and thereby the dispersive effect is achieved. Alternatively, the dispersive, focusing element may be constituted by a combination of refractive lenses, together acting as a positive lens, even if one or more lenses of the combination may be negative. In this case, the focal distance of the combination varies with the wavelength of incident light. By choosing a suitable combination of materials in the combination it is possible to adjust its dispersion in order to balance the change of optical length of the resonator due to wavelength changes, and hence provide a resonator without mode hops. Moreover, the dispersive, focusing element may be constituted by one refractive and one diffractive element. This may for example be provided by means of a lens, having one refractive surface and an opposite refractive surface with a diffractive surface relief. Such an element may also be provided as a refractive lens element and a separated diffractive element, which for example may be arranged as a diffractive surface relief on an element carrying the second reflecting end (such as a glass plate on one surface having the diffractive surface relief and on the opposite surface being provided with a mirror). Such a separate diffractive element may also be separated from the second reflecting end. It shall however be noted that a certain distance must be present between the second end and the diffractive surface relief in order to achieve the desired functionality. In the case of a non-rectilinear cavity geometry, such as a folded cavity, the dispersive focusing element may be provided as a focusing, reflecting surface, being provided with a diffractive surface relief. As yet an alternative, the dispersive focusing element may be arranged as so called GRIN element (Gradient Index element), preferably being provided with a diffractive surface relief on one of its surfaces. As another alternative, the dispersive focusing element may be constituted as a diffractive surface relief on a plane or curved surface being a part of a body carrying the reflecting end 2. Moreover, it is possible to utilise a holographic optical element as the dispersive focusing element, either alone or in combination with any one of the alternatives mentioned above. Also other combinations of the alternatives mentioned above are possible.

Regarding the dispersive focusing elements described above, it shall be noted that the measurement device will be able to resonate at different wavelengths as soon as the focusing element has an adequate dispersion, irrespective of the sign of the dispersion. However, in some cases mode-hopping may be an issue. A measurement device free of mode-hopping may be obtained by balancing the dispersion in such a way that the resonator Q value is the largest for the wavelength dependent resonator length that corresponds with a constant phase shift within the resonator. The dispersion shall be chosen such that the waist of a mode is moved with the same velocity as the stretch of the nodal pattern along the optical axis of the cavity. The velocity of movement of the waist in relation to the wavelength may be controlled by, for a certain lens dispersion, regulating the distance between the optical gain element and the dispersive focusing element.

Hence, in accordance with the present invention, a measurement device is achieved, which device has a resonant interval, i.e. measurement interval, which is only limited by the spectral width of the optical gain element. In contrast, if a dispersive focusing element is not used, a measurement device is achieved, which device only exhibits a narrow, limited resonant interval (in an order of magnitude of about one free spectral width of the resonator).

Figure 9A:
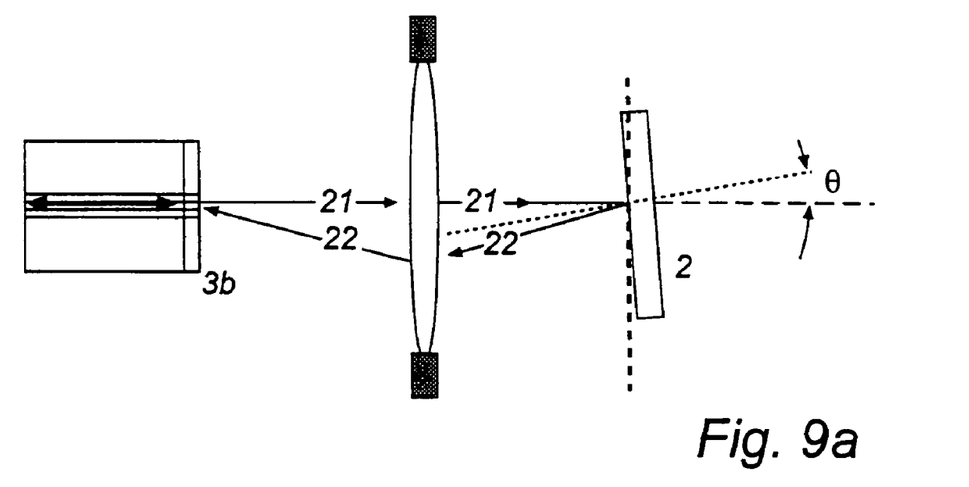
FIGS. 9a–9b schematically show multiple roundtrip paths of a beam that circulates in a resonator of a measurement device according to the invention.
Figure 9B:
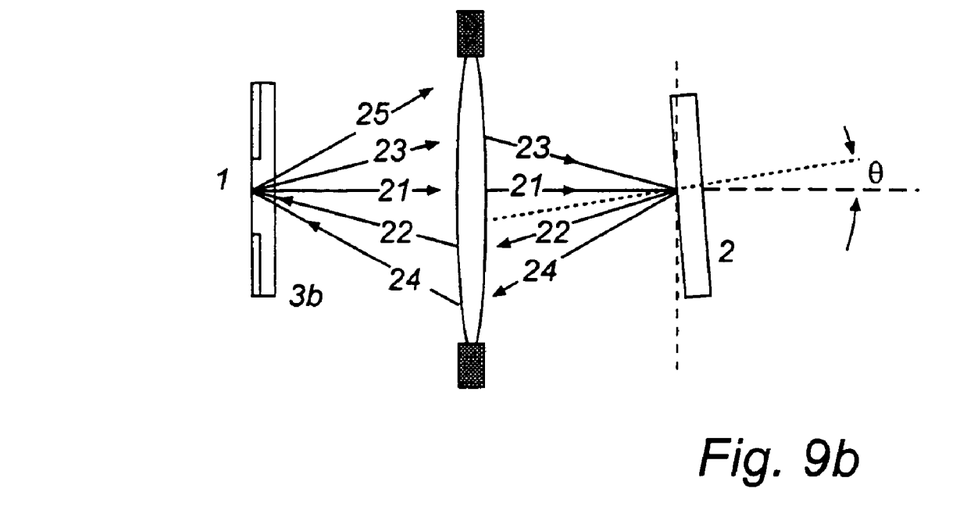

It shall also be noted that by the inventive arrangement, when using an edge emitting semiconductor gain element, the second end of the optical gain element is imaged on the second reflecting end of the resonator, and when using a surface emitting semiconductor gain element, the first reflecting end is imaged on the second reflecting end of the resonator, said imaging making the resonator arrangements stable. Hence, any object point on one mirror plane is imaged on the other mirror plane. This principle is illustrated in FIG. 9a for the case of using an edge emitting semiconductor gain element, where the reflective end 2, for example the measurement object, is angularly misaligned. A ray labelled 21 in FIG. 9a hits a reflective end 2 and is redirected back into the resonator along the beam path labelled 2. When the ray labelled 22 reaches the surface 3b, the mode is convolved with a waveguide mode of the optical gain element and continues towards the first reflecting end 3a and is reflected within the optical gain element and is again incident on the surface 3b, whereafter the above is repeated. This may be seen as if the circulating resonator mode is spatially filtered in the waveguide/gain element, once per round trip in the resonator. In the case of using a surface emitting semiconductor gain element, the stability of a resonator with an angularly misaligned reflection end 2 is illustrated in FIG. 9b, showing a ray labelled 21–25 redirected in the resonator. The basic principle is essentially the same as described with reference to FIG. 9a above.

Thus, due to the fact that any object point on the first reflecting end, or the second end of the optical gain element, as the case may be (see above), is imaged on the second reflecting end (and reversed), the resonator of the measurement device is very stable and insensitive to misalignments.

It shall further be noted that the end surface 3b of the gain element may or may not be provided with an anti-reflection coating. In a case where the surface 3b has a reflectivity, the main resonator comprises two coupled resonators, one being defined by the surfaces 3a and 3b, and one defined by the surface 3b and the reflecting end 2. This results in that the monotone measurement signal obtained also comprises a periodical variation. The variation is caused by the surface 3b. The periodicity may be controlled by selection of dispersion of the dispersive focusing element.

Finally, it shall be noted that many other modifications and alterations of this invention and its components are obvious for a man skilled in the art, when studying this disclosure and the appended claims.

For example, the first end surface of the optical gain element and the first reflecting end of the resonator in the above embodiments may be separated, whereby the first end surface in that case may be provided with an anti-reflection coating.

Also, although the optical gain element in the above embodiments is a semiconductor gain element, the optical gain element may be manufactured from a variety of materials, such as semiconductor materials, doped waveguide materials, such as erbium doped optical fibres, or doped solid state crystals.

Further, the measurement device may have a non-rectilinear cavity geometry, such as a folded cavity.

The invention claimed is:

1. A measurement device, for optically measuring a property of a measurement object, the measurement device comprising:
   a main resonator, having a first and a second reflecting end, defining a cavity having an effective optical cavity length,
   an optical gain element, for generating light travelling along an optical beam path between said first and second reflecting ends,
   a dispersive focusing diffractive resonator element, being positioned along the optical beam path between said optical gain element and said second reflecting end,
   whereby the measurement object is arranged to be at least partly positioned within the optical beam path of said main resonator,
   whereby the measurement device further comprises a detection means, for detecting a characteristic of light emitted from said main resonator, the value of the detected characteristic being a measure of a property of said measurement object.

2. A measurement device as in claim 1, wherein the characteristic of light to be detected by said detection means is at least one of the wavelength, the power, the polarisation or the phase of the light emitted from said main resonator.

3. A measurement device as in claim 1, wherein said measurement object is a solid object.

4. A measurement device as in claim 1, wherein the reflecting end is constituted by said measurement object.

5. A measurement device as in claim 4, wherein said measurement object and the rest of the measurement device is arranged to be moved in relation to each other in a direction essentially perpendicular to the direction of the optical beam being reflected by said measurement object.

6. A measurement device as in claim 5, wherein said detection means is arranged to detect a surface relief present on said measurement object.

7. A measurement device as in claim 1, wherein said measurement object is one of a gas, a liquid or a particle aerosol.

8. A measurement device as in claim 7, wherein said measurement object is arranged to flow through the optical beam path of said main resonator, thereby affecting the effective optical cavity length.

9. A measurement device as in claim 1, wherein said measurement device further comprises an adjustable driver for energising said optical gain element with variable drive current.

10. A measurement device as in claim 9, wherein said measurement device further comprises a current detection device, for detecting the current used by said driver to energise said optical gain element.

11. A measurement device as in claim 1, wherein said optical gain element has a first and a second opposing end surface, said second surface being positioned within said main resonator.

12. A measurement device as in claim 1, wherein the light emitted from the main resonator is emitted from at least one of said reflecting ends.

13. A measurement device as in claim 1, wherein the dispersion of the resonator element is chosen such that a waist of a mode is moveable.

14. A measurement device as in claim 1, wherein the resonator element includes a diffractive structure.

15. A measurement device, for optically measuring a property of a measurement object, the measurement device comprising:
   a main resonator, having a first and a second reflecting end, defining a cavity having an effective optical cavity length,
   an optical gain element, for generating light travelling along an optical beam path between said first and second reflecting ends,
   a dispersive focusing resonator element, being positioned along the optical beam path between said optical gain element and said second reflecting end,
   whereby the measurement object is arranged to be at least partly positioned within the optical beam path of said main resonator,
   whereby the measurement device further comprises a detection means, for detecting a characteristic of light emitted from said main resonator, the value of the detected characteristic being a measure of a property of said measurement object,
   wherein the dispersion of the resonator element is chosen such that a waist of a mode is moveable.

16. A measurement device as in claim 15, wherein the resonator element includes a diffractive structure.

* * * * *